US00RE36811E

United States Patent [19]

Markell et al.

[11] E Patent Number: Re. 36,811

[45] Reissued Date of Patent: Aug. 8, 2000

[54] SOLID PHASE EXTRACTION MEDIUM

[75] Inventors: Craig G. Markell, White Bear Township, County of Ramsey; Donald F. Hagen, Woodbury; James D. Luedtke, St Paul, all of Minn.

[73] Assignee: Minnesota Mining and Manufacturing Co., St. Paul, Minn.

[21] Appl. No.: 08/298,746

[22] Filed: Oct. 24, 1994

Related U.S. Patent Documents

Reissue of:

[64] Patent No.: 5,279,742
Issued: Jan. 18, 1994
Appl. No.: 08/930,714
Filed: Aug. 14, 1992

U.S. Applications:

[63] Continuation-in-part of application No. 07/651,791, Feb. 7, 1991, abandoned.

[51] Int. Cl.[7] ..... B01D 15/04

[52] U.S. Cl. ..... 210/638; 210/502.1; 210/505

[58] Field of Search ..... 210/198.3, 658, 210/505, 502.1, 489, 490, 692, 638; 427/245, 246; 264/120

[56] References Cited

U.S. PATENT DOCUMENTS

| | | | |
|---|---|---|---|
| 4,153,661 | 5/1979 | Ree et al. | 264/120 |
| 4,208,194 | 6/1980 | Nelson | 55/385.4 X |
| 4,373,519 | 2/1983 | Errede et al. | 128/156 |
| 4,460,642 | 7/1984 | Errede et al. | 428/283 |
| 4,512,897 | 4/1985 | Crowder, III et al. | 210/656 |
| 4,565,663 | 1/1986 | Errede et al. | 264/120 |
| 4,722,898 | 2/1988 | Errede et al. | 435/182 |
| 4,810,381 | 3/1989 | Hagen et al. | 210/502.1 |
| 4,871,671 | 10/1989 | Errede et al. | 439/182 |
| 4,906,378 | 3/1990 | Hagen et al. | 210/635 |
| 4,935,142 | 6/1990 | Sternberg | 210/634 |
| 4,971,697 | 11/1990 | Dowden et al. | 210/502.1 |
| 4,971,736 | 11/1990 | Hagen et al. | 264/22 |
| 5,009,869 | 4/1991 | Weinberg | 204/180.1 X |
| 5,019,232 | 5/1991 | Wilson et al. | 204/180.1 X |

FOREIGN PATENT DOCUMENTS

| | | |
|---|---|---|
| 59-142845 | 8/1984 | Japan . |
| 61-54237 | 3/1986 | Japan . |
| 2024886 | 1/1980 | United Kingdom . |

OTHER PUBLICATIONS

Life Science Research Products (BioRad) Price List R (Jan. 1992).

American Biotechnology Laboratory, Oct. 1988, pp. 26–32.

Chromatography Electrophoresis Immunochemistry Molecular Biology HPLC (BioRad) Price List O (Mar. 1989).

Chromatography Electrophoresis Immunochemistry Molecular Biology HPLC (BioRad) Price List P (Mar. 1990).

Life Science Research Products (BioRad) Price List Q (Mar., 1991).

Hagen et al., *Analytical Chimica Acta,* 236 (1990) pp. 157–164.

Design News, Feb. 9, 1987, Cahners Publishing Company.

L. A. Errede, *Journal of Applied Polymer Science*, 31 (1986) pp. 1749–1761.

L. A. Errede, et al., *Chemically Modified Surfaces in Science and Industry*, 2, Proceedings of the Chemically Modified Surfaces Symposium, Fort Collins, Colo. (1987), pp. 91–104, Gordon and Breach Science Publishers, N.Y.

*Primary Examiner*—Ana Fortuna
*Attorney, Agent, or Firm*—Gary L. Griswold; Robert W. Sprague; William J. Bond

[57] ABSTRACT

A method for isolating an environmentally hazardous organic contaminant from a fluid utilizes a solid phase extraction medium comprises a PTFE fibril matrix, and sorptive particles enmeshed in said matrix comprising more than 30 and up to 100 weight percent of porous organic particles, and less than 70 to 0 weight percent of porous (organic-coated or uncoated) inorganic particles, the ratio of sorptive particles to PTFE being in the range of 40:1 to 1:4 by weight. The extraction medium is useful in pesticide, phenolics, and residue of explosives separations. The separations can be efficiently performed in a stacked disk format.

46 Claims, 1 Drawing Sheet

SOLID PHASE EXTRACTION MEDIUM

Matter enclosed in heavy brackets [ ] appears in the original patent but forms no part of this reissue specification; matter printed in italics indicates the additions made by reissue.

This is a continuation-in-part of Ser. No. 651,791, filed Feb. 7, 1991, now abandoned.

FIELD OF THE INVENTION

This invention relates to a method of isolating environmentally hazardous organic materials such as pesticides, phenolics, and residues from explosives from gases or aqueous or organic solution. The method uses solid phase extraction media which comprise a polytetrefluoroethylene (PTFE) fibril matrix in which are enmeshed sorptive particles. In another aspect, a novel article and stacked article for use as an extraction medium is disclosed.

BACKGROUND OF THE INVENTION

Extraction and chromatographic media and processes, which can be broadly described as separation science, are known in the art. They provide a means of isolating, separating, and analyzing mixtures of solutions by selective adsorption on materials such as nylon, alumina, silica, and bonded silica. The process is based on differences in the distribution ratios of the components of mixtures between a mutually immiscible mobile and a fixed stationary phase. In thin layer chromatography, it is known to use thin films, such as silica mixed with a binder (e.g. calcium sulfate) adhered to glass for the separating vehicle. In particular, there are formed isolated spots or bands which can be separated mechanically and further examined.

U.S. Pat. No. 4,153,661 discloses a method of making a polytetrafluoroethylene composite sheet comprising a PTFE matrix with particulate material, which is substantially insoluble in water, dispersed therein. The resulting sheet is extremely pliable, akin to doe skin. It is said to be useful as an electronic insulator or a semi-permeable membrane U.S. Pat. No. 4,373,519 discloses a composite wound dressing comprising a PTFE matrix with water-swellable hydrophilic absorptive particles enmeshed in the matrix, and, optionally, a partially occlusive film coated on one surface of the matrix. It is disclosed that the particulate material can account for from 40 to 90% by weight of the total composition, of which up to 50% can be inert property modifier particles. Examples of property modifier particles include silica, kaolin, talc, bentonite, vermiculite, etc. The sheets are described as conformable and chamois-like.

U.S. Pat. Nos. 4,565,663 and 4,460,642, which are related to U.S. Pat. No. 4,373,519, disclose water-swellable composite sheets having a PTFE matrix in which water-swellable hydrophilic absorptive particles are enmeshed. As in U.S. Pat. No. 4,373,519, the water-swellable particulate can account for from 40 to 90% by weight of the total composition, of which up to 50% by weight can be inert property modifier particles, e.g. silica. The sheets are described as conformable and chamois-like. It is disclosed that they can be used as chromatographic materials. It is also disclosed that certain water-swellable cation exchange resins can be used in chromatographic applications.

U.S Pat. No. 4,810,381, U.S. Pat. No. 4,906,378, and U.S. Pat. No. 4,971,736 disclose composite articles comprising a PTFE fibril matrix in which is enmeshed non-swellable particulate. The articles are useful in chromatographic applications. Up to 30 weight percent of total particulate can be property modifier particles which include polymethacrylates, styrene-divinylbenzene copolymers, and silica coated with polyacrylamide. Stacked layers of identical composition are disclosed as a means of increasing path length.

Hagen et al., Analytical Chimica Acta, 236 (1990) 157–164, disclose a method using hydrophobic $C_8$- and $C_{18}$-bonded silica particles enmeshed in a PTFE membrane as an alternative to using particle packed columns for solid phase extraction (SPE) applications.

Highly crosslinked copolymeric particles of styrene and divinylbenzene (XAD™ nonionic polymeric adsorbents) and highly crosslinked methacrylic copolymeric particles (Amberchrom™) polymeric adsorbants are available commercially from Supelco, Inc., Bellefonte, Pa. Octadecyl-bonded silica particles, another type of adsorbent, are available from Varian Sample Preparation Products, Harbor City, Calif.

SUMMARY OF THE INVENTION

Briefly, the present invention provides a method of isolating at least one environmentally hazardous organic contaminant from a fluid comprising the step of passing a fluid containing at least one organic contaminant through at least one solid phase extraction medium comprising (a) a PTFE fibril matrix, and (b) sorptive particles enmeshed in said matrix comprising (1) more than 30 and up to 100 weight percent of porous organic particles, and (2 ) less than 70 to 0 weight percent of porous, organic-coated or uncoated inorganic particles, the ratio of sorptive particles to PTFE being in the range of 40:1 to 1:4, preferably 19:1 to 4:1, by weight.

In a further step, the contaminant can be isolated by elution from the extraction medium.

In another aspect, a solid phase extraction medium and a stack of such media are disclosed as useful in applications in separations science.

In a further aspect, there is disclosed a unique method of stacking solid phase extraction media of the present invention wherein the particulate in one medium can be the same or different composition from particulate in other media of the stack.

In this application:

"polar" means at least one of hydrophilic and water-soluble;

"water-soluble" means greater than 1.0 g dissolves in 100.0 g of water at 20° C.;

"semi-polar" means in the range of 0.01 g to 1.0 g dissolves in 100.0 g of water at 20° C.;

"non-polar" means less than 0.01 g dissolves in 100.0 g of water at 20° C.;

"matrix" means an open-structured entangled mass of microfibers;

"hydrophobic particles" mean particles with low surface polarity, i.e. in the range of 0.1–0.5;

"hydrophilic particles" mean particles having high surface polarity (i.e., greater than 0.5);

"fluid" means a gas or liquid;

"ceramic" means nonmetallic, inorganic materials;

"direct phase system" means a more polar stationary phase with a less polar moving phase;

"reverse phase system" means a less polar stationary phase with a more polar moving phase;

"non-swellable particulate" means particulate having a change in volume, wherein $$\text{change in volume} = \frac{V_g - V_o}{V_o}.$$

of less than 0.5, preferably less than 0.1, most preferably less than 0.01, where $V_g$ is the volume of the particulate when swollen and $V_o$ is the volume of the dry particulate; swellability correlates inversely with degree of crosslinking in polymers; preferred particulate are non-swellable and have correspondingly high crosslinked density;

"particles" or "particulate" means fibers of diameter 1 to 100 micrometers, with a length to diameter ratio of 1 to 20, in addition to particles such as granules, beads, or powders as defined below;

"self-supporting" means that no rigid backing support is needed for the article; and "sorbent" "sorb", or "sorptive" means capable of taking up and holding by either absorption or adsorption.

Use of media of the invention containing polymeric resin particles in the form of extraction disks shows:

(1) surprising advantages in using porous organic particles in a PTFE matrix over sole use of organic-bonded silica particles in a PTFE matrix in that much higher extraction efficiencies are obtained especially for polar and semi-polar contaminants, such that no additives to the water such as salt or acid are necessary, making a simpler method of analysis while giving quantitative recoveries. Also, the capacity of such a disk for organic compounds is at least 3 times greater when compared to bonded silica disks;

(2) advantageous use of stacked disks, both of the same composition and different compositions, as a way of increasing capacity, percent recovery, and/or differentiating compounds depending on their polarity;

(3) utility of disks with a blend of different particles, which can have some of the advantages of each of several types of particles.

Resin particles, in contrast to coated or bonded particles, are particularly useful for the more polar contaminants. Resin particles such as copolymers of styrene-divinylbenzene and polymers of (meth)acrylic acid esters or polymers of divinylbenzene show increased percent recoveries, i.e., increased extraction efficiency compared to $C_{18}$-bonded silica used alone.

It is believed novel in the art to incorporate styrene-divinyl benzene polymeric particles in a PTFE fibrillated matrix for use to isolate contaminant organic compounds from fluids. These particles in a PTFE fibrillated matrix provide superior separatory capabilities. It has been found that the kinetics of diffusion allows processing of fluids and removal of contaminants at a much faster rate for equivalent or better recoveries using a composite article compared to state-of-the-art packed columns or beds of particles.

DETAILED DESCRIPTION OF PREFERRED EMBODIMENTS

Figure 1:
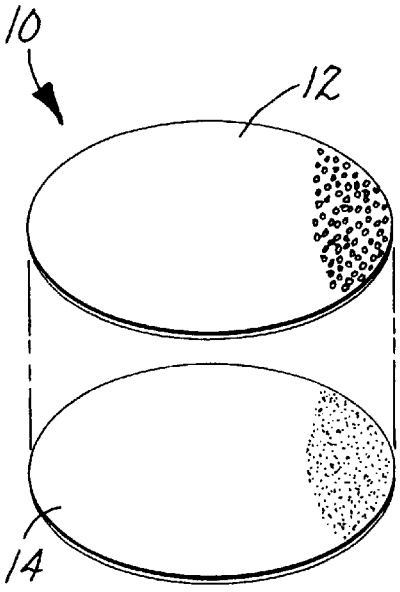
FIG. 1 shows a stack of two disks, each being an extraction medium of the invention.

Particulate material (which can be one material or a combination of materials) useful in the present invention is substantially insoluble in aqueous liquid and organic liquid such as water and ethyl acetate and in the elution liquid. Not more than 1.0 gram of particulate will dissolve in 100 g. of aqueous or organic liquid or elution solvent into which particulate is mixed at 20° C. The particulate material can be at least one of an organic polymer such as polydivinylbenzene, or a copolymer, preferably a copolymer of styrene and divinylbenzene (75–25 to 99.99–0.01), or poly(meth)acrylic acid esters, and derivatives thereof, particularly those containing ion-exchange groups such as sulfonated or aminated groups.

Suitable optional particles for the purposes of this invention include any particle which can be coated with aqueous- or organic-insoluble, non-swellable sorbent material or the surface (external and/or internal) of which can be derivatized to provide a coating of insoluble, non-swellable sorbent material. Optional particles include inorganic oxide particles such as silica, alumina, titania, zirconia, and other ceramics to which are covalently bonded organic groups. Preferred inorganic oxide particulate materials are silica and zirconia because they are commercially available, with silica being particularly preferred because of the ease in bonding a variety of hydrophobic and hydrophilic ligands and coatings onto its surface.

The insoluble, aqueous non-swellable sorbent coatings generally have a thickness in the range of one molecular monolayer to about 100 nanometers. Such particles having coated surfaces are well known in the art, see, for example, Snyder and Kirkland, "Introduction to Modern Liquid Chromatography", 2d Ed., John Wiley & Sons, Inc. (1979) and H. Figge et al., "Journal of Chromatography" 351 (1986) 393–408 and include modified silica particulate, silica particles having covalently bonded thereto organic groups, preferably cyanopropyl, cyclohexyl, phenyl, $C_2$ (ethyl), $C_4$ (butyl), $C_8$ (octyl), and $C_{18}$ (octadecyl) groups.

Coatings which can be applied to inorganic particulate can be either thin mechanical coatings of insoluble, non-swellable polymers such as crosslinked silicones, polybutadienes, etc. or covalently bonded organic groups such as aliphatic groups of varying chain length (e.g., $C_2$, $C_4$, $C_8$, and $C_{18}$) and organic groups including aliphatic and aromatic groups. Preferred groups include amino, cyano, hdyroxyl, phenyl, cyclohexyl, chiral, and other groups which alter the polarity of the coating. The silica, or other support particle, in this case acts primarily as a carrier for the organic coatings and the particles are non-swellable. Many such coated particles are commercially available (e.g., $C_{18}$ bonded phase silica, Alltech, Deerfield, Ill., or Varian Sample Preparation Products, Harbor City, Calif.). Variation in chemical composition of the coatings can provide selectivity in molecular separations and polarity.

Particularly preferred particulate for use in the present invention include:

| Material | Particle size | Trademark | Available from |
|---|---|---|---|
| highly crosslinked styrene and divinylbenzene copolymers, high performance material* | 50–100 micrometers | Amberchrom ™ CG-161m | Supelco, Inc., Bellefonte, PA |
| highly crosslinked methacrylic resin, high performance material* | 50–100 micrometers | Amberchrom ™ CG-71m | Supelco, Inc., Bellefonte, PA |
| highly crosslinked styrene and divinylbenzene copolymer* | 220–830 micrometers (ground to average size about 50 micrometers) | Amberlite ™ XAD-2 | Supelco, Inc., Bellefonte, PA |
| highly crosslinked methacrylic copolymer* | 220–830 micrometers (ground to average size about 50 micrometers) | Amberlite ™ XAD-7 | Supelco, Inc., Bellefonte, PA |
| octadecyl-bonded silica | 8 micrometers | $C_{18}$ ™ | Varian Sample Preparation Products, Harbor City, CA |

*Disclosed in one or more of U.S. Pat. Nos. 4,501,826; 4,382,124; 4,297,220; 4,256,840; 4,224,415

Any of the particulate material may have a spherical shape, a regular shape or an irregular shape. Particulate material which has been found useful in the invention has an apparent size within the range of 0.1 to about 150 micrometers, preferably in the range of 0.1 to 100 micrometers, more preferably 1 to 100 micrometers. It has been found advantageous in some instances to employ particulate materials in two or more particle size ranges falling within the broad range. As an example, particles having an average size in the range of 0.1–30 micrometers having chromatographic activity may be employed in combination with particles having an average size in the range 1 to 150 micrometers acting as a property modifier.

Some particle size reduction may take place during high shear mixing and calendering operations, depending upon the friability of the particulate material. Thus, while the particulate material initially may be rather large, it may ultimately be reduced to a finer size in the final product. In some instances, particle size reduction may be necessary before mixing.

Particles useful in the present invention have water sorptive capacity less than 25% by weight, preferably less than 5% by weight, compared to particle weight. As noted above, particles which undergo dimensional changes due to water swellability are less desirable because they can cause dimensional changes, such as wrinkling, in the article.

More than one type of active sorbent particles useful in the present invention can be pre-mixed in any proportion, the total sorptive particules being present in the range of more than 30 up to 100 weight percent of at least one of organic polymeric particles, preferably 35 to 100 weight percent, more preferably 50 to 100 weight percent organic polymeric particles, and 0 to 70 weight percent of total particulate of porous organic-coated or uncoated inorganic particles, preferably 0 to 65 weight percent, and more preferably 0 to 50 weight percent porous organic-coated or uncoated inorganic particles.

Other non water-swellable property modifiers may be advantageously added to the mixture of the PTFE aqueous dispersion and the primary particulate material to provide further improvement in or modification of the composite articles of the invention. For example, modifier particulate can include chromatographically inactive materials such as low surface area glass beads to act as property modifiers and processing aids. Coloring or fluorescing particulate can be added at low levels (up to 10 weight percent of particulate) to aid in visualizing sample components to be separated. Chemically active particulate which indicate pH or acidity of the component bands can be useful for diagnostic purposes.

A limited amount of water-swellable property modifiers (i.e., up to 30 weight percent, preferably less than 25 weight percent, more preferably less than 10 weight percent, and most preferably less than 1 weight percent, of total particulate) can be useful as a processing aid. Representative swellable property modifiers include starch, chitosan, modified starches such as Sephadex™ and Sepharose™ (pharmacia, Sweden), agarose, polyacrylamides, cellulosics, and coated particles (e.g., silica coated with a polyacrylamide). Water-swellable but insoluble materials may be used as a thin coating on non-swellable particulate.

When the particulate is hydrophobic, the preferred method of manufacture of the article of the invention utilizes an emulsion of PTFE with a masking agent added to modify the hydrophobic particle surface/water interaction and to allow rapid wetting of the surface of the hydrophobic particulate. Preferred masking agents are polar organic compounds such as alcohols, amines, acids, etc. with the preferred agent being alcohols due to their efficacious removability as by solvent extraction or drying after formation of the article.

Specifically, the PTFE composite sheet material of the invention is prepared by blending the particulate or combination of particulates employed with a PTFE emulsion until a uniform dispersion is obtained and adding a volume of process lubricant up to approximately one half the volume of the blended particulate. Blending takes place along with sufficient process lubricant to exceed sorptive capacity of the particles in order to generate the desired porosity level of the resultant article. Preferred process lubricant amounts are in the range of 3 to 200 percent by weight in excess of that required to saturate the particulate, as is disclosed in U.S.

Pat. No. 5,071,610. The aqueous PTFE dispersion is then blended with the particulate/masking agent mixture to form a mass having a putty-like or dough-like consistency. The sorptive capacity of the solids of the mixture is noted to have been exceeded when small amounts of water can no longer be incorporated into the mass without separation. Care should be taken to ensure that the ratio of water to masking agent does not exceed 3:1. This condition should be maintained throughout the entire mixing operation. The putty-like mass is then subjected to intensive mixing at a temperature and for a time sufficient to cause initial fibrillation of the PTFE particles. Preferably, the temperature of intensive mixing is up to 90° C., preferably it is in the range of 0° to 90° C., more preferably 20° to 60° C. Minimizing the mixing at the specified temperature is essential in obtaining extraction media and chromatographic transport properties.

Mixing times will typically vary from 0.2 to 2 minutes to obtain the necessary initial fibrillation of the PTFE particles. Initial mixing causes partial disoriented fibrillation of a substantial portion of the PTFE particles.

Initial fibrillation generally will be noted to be at an optimum within 60 seconds after the point when all components have been fully incorporated into a putty-like (dough like) consistency. Mixing beyond this point will produce a composite sheet of inferior extraction medium and chromatographic properties.

Devices employed for obtaining the necessary intensive mixing are commercially available intensive mixing devices which are sometimes referred to as internal mixers, kneading mixers, double-blade batch mixers as well as intensive mixers and twin screw compounding mixers. The most popular mixer of this type is the sigma-blade or sigma-arm mixer. Some commercially available mixers of this type are those sold under the common designations Banbury mixer, Mogul mixer, C. W. Brabender Prep mixer and C. W. Brabender sigma blade mixer. Other suitable intensive mixing devices may also be used.

The soft putty-like mass is then transferred to a calendering device where the mass is calendered between gaps in calendering rolls preferably maintained at a temperature up to 125° C., preferably in the range of 0° to about 100° C., more preferably in the range of 20° to 60° C., to cause additional fibrillation of the PTFE particles of the mass, and consolidation while maintaining the water level of the mass at least at a level of near the sorptive capacity of the solids, until sufficient fibrillation occurs to produce the desired extraction medium. Preferably the calendering rolls are made of a rigid material such as steel. A useful calendering device has a pair of rotatable opposed calendering rolls each of which may be heated and one of which may be adjusted toward the other to reduce the gap or nip between the two. Typically, the gap is adjusted to a setting of 10 millimeters for the initial pass of the mass and, as calendering operations progress, the gap is reduced until adequate consolidation occurs. At the end of the initial calendering operation, the resultant sheet is folded and then rotated 90° to obtain biaxial fibrillation of the PTFE particles. Smaller rotational angles (e.g., 20° to less than 90°) may be preferred in some extraction and chromatographic applications to reduce calender biasing, i.e., unidirectional fibrillation and orientation. Excessive calendering (generally more than two times) reduces the porosity which in turn reduces the solvent wicking rate in TLC and the flow-through rate in the filtration mode.

During calendering, the lubricant level of the mass is maintained at least at a level of exceeding the absorptive capacity of the solids by at least 3 percent by weight, until sufficient fibrillation occurs and to produce porosity or void volume of at least 30% and preferably 40 to 70% of total volume. The preferred amount of lubricant is determined by measuring the pore size of the article using a Coulter Porometer as described in the Examples below. Increased lubricant results in increased pore size and increased total pore volume as is disclosed in U.S. Pat. No. 5,071,610.

The calendered sheet is then dried under conditions which promote rapid drying yet will not cause damage to the composite sheet or any constituent therein. Preferably drying is carried out at a temperature below 200° C. The preferred means of drying is by use of a forced air oven. The preferred drying temperature range is from 20° C. to about 70° C. The most convenient drying method involves suspending the composite sheet at room temperature for at least 24 hours. The time for drying may vary depending upon the particular composition, some particulate materials having a tendency to retain water more than others.

The resultant composite sheet preferably has a tensile strength when measured by a suitable tensile testing device such as an Instron (Canton, Mass.) tensile testing device of at least 0.5 MPa. The resulting composite sheet has uniform porosity and a void volume of at least 30% of total volume.

The PTFE aqueous dispersion employed in producing the PTFE composite sheet of the invention is a milky-white aqueous suspension of minute PTFE particles. Typically, the PTFE aqueous dispersion will contain about 30% to about 70% by weight solids, the major portion of such solids being PTFE particles having a particle size in the range of about 0.05 to about 0.5 micrometers. The commercially available PTFE aqueous dispersion may contain other ingredients, for example, surfactant materials and stabilizers which promote continued suspension of the PTFE particles.

Such PTFE aqueous dispersions are presently commercially available from Dupont de Nemours Chemical Corp., for example, under the trade names Teflon™ 30, Teflon™ 30B or Teflon™ 42. Teflon™ 30 and Teflon™ 30B contain about 59% to about 61% solids by weight which are for the most part 0.05 to 0.5 micrometer PTFE particles and from about 5.5% to about 6.5% by weight (based on weight of PTFE resin) of non-ionic wetting agent, typically octylphenol polyoxyethylene or nonylphenol polyoxyethylene. Teflon™ 42 contains about 32 to 35% by weight solids and no wetting agent but has a surface layer of organic solvent to prevent evaporation. It is generally desirable to remove, by organic solvent extraction, any residual surfactant or wetting agent after formation of the article.

Silica is available from Aldrich Chemical Co. (Milwaukee, Wis.). Zirconia is available from Z. Tech Corporation (Bow, N.H.). Other inorganic oxides are commercially available (Aldrich Chemical Co.).

The present invention provides a novel composite structure and method therefore, the composite structure preferably being a uniformly porous, composite sheet comprised of non water-swellable sorptive particles distributed uniformly throughout a matrix formed of interentangled, fibrillated PTFE fibrils. In such a structure almost all of the particles are separate one from another and each is isolated in a cage that restrains the particle on all sides by a fibrillated mesh of PTFE microfibers. The preferred novel sheet of the invention has a thickness in the range of 125 to 10,000 micrometers and preferably has a tensile strength of at least 0.5 MPa and even as high as 13.6 MPa. The article is substantially uniformly porous, making it suited for use in separation science. More particularly, it can be used in solid phase extraction, and as a chromatographic composite article which can be used as a single self-supporting sheet or a combination of sheets to form a stack or as a composite film adhered to a support such as glass, paper, metals, or polymers.

The PTFE-particulate media technology can be useful in a first mode wherein the composite article of the invention is used for preconcentration and isolation of certain materials for further analysis by high resolution column chromatography. In this mode, which is well known in the art and commonly called solid phase extraction, solvent and sample flow are introduced at an angle of 90 degrees to the surface of the sheet. This is a conventional configuration and the separation path length is equal to the thickness of the sheet. The path length can be increased by stacking additional layers (media) which may be the same or of different composition but the individual layers are not intimately bound together. This mode is effective for one step or multi step adsorption- desorption separations. This mode is effective using reactive particulate such as non-swellable ion exchange materials or sorptive particulate in the direct or reverse phase modes. The article strongly adsorbs the component of interest onto the active (non-swellable) particulate in the composite and undesirable components are washed out with a first solvent. A more effective eluting solvent is then used to displace the desired component from the particulate allowing it to be recovered in a more concentrated and unified form.

the composite extraction and chromatographic articles of the invention can be of a variety of sizes and shapes. Preferably the articles can be sheet-like materials which, for example, can be in disk or strip form.

The composite articles have utility in a wide variety of separations wherein the choice of the particulate material is useful for size controlled filtration or steric exclusion, for simple one step or multistep adsorption-desorption separations of specific components, for immobilization of particulate to perform ion-exchange conversion and isolation of cations and anions, for purification of materials, and for chromatographic separations and analyses in both passive and forced flow modes, for hydrophobic reverse phase and direct phase chromatography.

This invention discloses the discovery of a solid phase extraction (SPE) disk/sheet composite material and a method which is effective, for example, in removing relatively polar compounds such as certain pollutants from liquid and gas samples. Solid phase extraction is a technique wherein solid particulate such as polymeric materials, silica, alumina, or zirconia, etc., coated with insoluble polymeric phases or covalently bonded organic ligands are used to preferentially adsorb organic compounds from liquids or gases for isolation purposes. Representative polar and semi-polar compounds described in the examples below are an explosive (1,3,5,7-tetranitro,- 1,3,5,7-tetraazacyclooctane) (HMX), an explosive impurity (dinitrotoluene), and a series of phenolic compounds such as phenol, o-cresol, 2-nitrophenol, 4,6-dinitro-o-cresol, 2,4-dichlorophenol, 2,4,5-trichlorophenol, and 2,4,6-trichlorophenol, which are pollutants in water and which are of environmental concern. Representative pesticides, generally considered semi-polar compounds, which can be recovered from aqueous liquids include atrazine, alachlor, and diazinon. These compounds are commonly extracted from water using liquid/liquid (LLE) extractions, described in EPA Method 608, 625, etc. It is highly desirable to replace liquid-liquid extraction (LLE) methods with solid phase extraction (SPE) materials and methodology to reduce or eliminate extraction solvent usage, extraction time, and environmental hazards. This invention discloses using a hybrid of column particle and membrane technologies to provide a means of overcoming the deficiencies of conventional methods with substantial savings in time and cost.

The extraction medium of the present invention is also useful to extract certain polar contaminants such as phenols from a nonpolar liquid such as hexane.

Solid phase extractions of polar compounds from water samples are known to result in low recoveries because of the unfavorable partition coefficients of the compounds between water and the conventional non-polar stationary solid phases such as $C_{18}$-bonded silica. This is particularly true when large volumes of water are used, where the volume of sample is larger than the breakthrough volume of the specific compound. Breakthrough volume is defined as that volume in which the capacity of the sorbent particle bed for a particular contaminant is exceeded allowing passage of the extractant without efficient sorption. More specifically, it is the volume at which the contaminant (extracted material) can be detected in the exit stream from the extraction medium. Prior art methods of overcoming the problem of inadequate recovery are: (1) to use smaller sample volumes of less than the breakthrough volume, (2) accept low recovery data, and designate the results as "semi-quantitative", or (3) include an additive in the water sample, such as sodium chloride, to shift the partition coefficient in favor of the solid phase. None of these solutions are particularly attactive. Ideally, polar compounds can be isolated using the same conditions as those used for the less polar pollutants, thus providing a universal SPE method and SPE media for many pollutants including the less polar pesticides, polychlorinated biphenyls (PCBs) and polynuclear aromatic hydrocarbons (PAHs) as well as the more polar pesticides, phenolics, and explosive residues.

It has been found advantageous where combinations of contaminants are to be extracted to use a stack of disks (e.g., 2 to 5 or more) with one or more types of particulate chosen, each having optimum extraction efficiency for individual contaminants. Choice of elution solvents depends on contaminants and extraction particulate.

In FIG. 1, stack of disks 10 contains disks 12 and 14 which can be identical or they can contain different particulate so as to have different selectivities for different contaminants.

Figure 2:
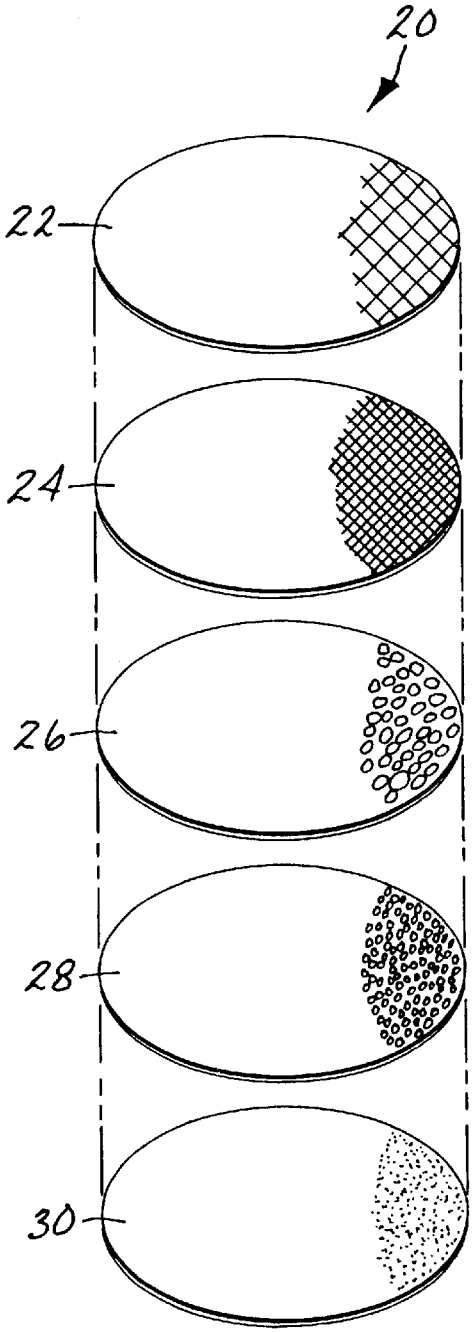
FIG. 2 shows a stack of five disks, each being an extraction medium of the invention.

In FIG. 2, similarly, stack of disks 20, made of disks 22, 24, 26, 28, and 30, each of which can be the same or can contain different particulate so as to provide an effective separations medium.

Extraction media of the present invention are particularly useful to isolate polar, semi-polar, and nonpolar organic contaminants from fluids (gases and liquids). In particular, residues of explosives, phenolic compounds, and organic acids are common contaminants of soil, air, water, and can be efficiently removed, concentrated, or isolated using the teachings of the present invention. The isolations can be performed on an analytical scale or in large scale applications.

Objects and advantages of this invention are further illustrated by the following examples, but the particular materials and amounts thereof recited in these examples, as well as other conditions and details, should not be construed to unduly limit this invention.

EXAMPLE 1

Data of this example show increased recoveries of contaminants in a solid phase extraction application using articles (disks) of the present invention compared to disks comprising conventional bonded silica particulates enmeshed in a PTFE matrix.

A. (comparative) A disk was prepared as follows: Ten grams of $C_{18}$ bonded silica (Analytichem Int., Harbor City, Calif.) was placed in a 100 ml beaker. This particle has a lubricant sorptive capacity approximately 75 percent of particle weight. 1.6 grams of polytetrafluoroethylene (PTFE) resin emulsion (Teflon™ 30B, E. I. Dupont, Inc., Wilmington, Del.) was added stepwise in three portions with intermittent vigorous stirring. This provided a $C_8$ bonded silica to PTFE ratio of 90/10. The temperature can be up to 90° C., preferably in the range of 0° to 90° C., more preferably about 23° C. Lubricant was added (10.5 grams) stepwise in three portions with intermittent vigorous stirring. After these ingredients have been thoroughly mixed, a semi-coherent material was formed with enough physical integrity to allow the entire contents of the beaker to be removed as a single mass. The above mass was passed between two rollers kept at 50° C. It is also possible to maintain the rollers up to 125° C., preferably 0° to 100° C., more preferably 20° to 60° C., and spaced about 0.5 cm apart to give a strip of cohesive material. The resulting strip was folded to three thicknesses and then passed through the rollers after a 90 degree rotation from the previous pass. The cyclic process of folding and re-rolling in a direction 90° from the direction of the previous pass was repeated multiple times to give a tough, strong, flat piece of material. The material was then calendered along the long axis via a series of roller passes with roller spacing adjusted to successively smaller distances apart to give a continuous ribbon. The ribbon was folded to give a multi-layer piece which was then calendered as before along the axis 90° from the calendering direction used previously.

The calendered sheet of material was then allowed to dry in air for 48 hours.

One hundred mL portions of reagent water were fortified individually with a set of compounds at concentations of from 0.5 to 20 mg/L (ppm), passed through the disks, which were then eluted with acetonitrile (to recover the concentrated contaminant compounds extracted from the water), and subsequently analyzed by high pressure liquid chromatography (HPLC). Data are shown in TABLE I, below. These results on disks of $C_{18}$-bonded silica particulate enmeshed in PTFE were the best obtained from several particulates, including cyano, cyclohexyl, and $C_8$-bonded silica ($C_{18}$-bonded and $C_8$-bonded silicas were available from Varian Sample Preparation Products, Harbor City, Calif.). The first column (A) shows the data obtained using no additives in the water, except the usual 0.5% (vol/vol) methanol/water used to promote "wetting" of the $C_{18}$-bonded silica disks. Second column (B) shows the data using the same disk, but with 3.5% (wt/vol) sodium chloride added to the water. Column C shows the data without sodium chloride but with the pH of the water adjusted to 2, and the data in column D show the effect of a pH of 2 and 25% (wt/vol) sodium chloride.

Data of TABLE I illustrate the positive effect of addition of sodium chloride to shift partitioning of the contaminant from the water to the solid phase sorbent particulate and adjustment of the pH to suppress ionization of the phenolics.

Recoveries of the explosive HMX and phenol were low from the 100 mL sample of water, even with high concentrations of salt and pH adjustment steps, indicating that breakthrough or incomplete sorption had occurred.

B. (present invention) Sorbent particles obtained from Supelco, Bellefonte, Pa., were incorporated into the PTFE matrix using the following procedure: To prepare disks the following procedure was used: Twenty grams of styrene divinylbenzene copolymer (Amberchrom CG-161m) were placed in a 100 ml beaker. Ten grams of polytetrafluoroethylene (PTFE) resin emulsion (Fluon™, ICI Americas, Inc., Wilmington, Del.) was added stepwise in three portions with intermittent vigorous stirring. This provided a copolymer to PTFE ratio of 90/10. The temperature can be up to 90° C., preferably in the range of 0° to 90° C., more preferably about 23° C. Fifty-five grams of lubricant (water/isoproanol 70/30) was added stepwise in three portions with intermittent vigorous stirring. After these ingredients had been thoroughly mixed, a semi-coherent material was formed with enough physical integrity to allow the entire contents of the beaker to be removed as a single mass. The above mass was passed between two rollers kept at 38° C. It is also possible to maintain the rollers up to 125° C., preferably 0° to 100° C., more preferably 20° to 60° C., and spaced about 0.5 cm part to give a strip of cohesive material. The resulting strip was folded to three thicknesses and then passed through the rollers after a 90 degree rotation from the previous pass. The cyclic process of folding and re-rolling in a direction 90° from the direction of the previous pass was repeated multiple times to give a tough, strong, flat piece of material. The material was then calendered along the long axis via a series of roller passes with roller spacing adjusted to successively smaller distances apart to give a continuous ribbon. The ribbon was folded to give a multi-layer piece which was then calendered as before along the axis 90° from the calendering direction used previously.

The calendered sheet of material was then allowed to dry in air for 24 hours.

The resulting disks, cut to the appropriate size from the sheet, were used for the extraction under the same conditions used for TABLE I, but without any additives to the water except 0.5% methanol.

The sorbent particles were Amberchrom™ CG-161m (Supelco, Bellefonte, Pa.), which is a relatively large-particle (50–100 um) styrene-divinyl benzene resin. 100 mL of water was extracted as shown above, but without acid or sodium chloride, 0.5% (vol/vol) methanol/water was added in all cases. Additionally, the usual acetonitrile elution was followed by two-1 mL ethyl acetate elutions of the disk. Ethyl acetate is less polar than acetonitrile and is a more effective eluting solvent than acetonitrile. Results of this trial are given in TABLE II, below. Data in column E is from Amberchrom CG-161m resin, 100 mL water samples with no salt or acid, extracted in 24 min. Data in column F is the same, but using 1000 mL water samples, extracted in 30 min. Data obtained and listed in columns G and H used the same volumes and conditions as E, but the 100 mL samples were passed through the 47 mm disk in 12 and 72 seconds, respectively.

In all cases, elution was accomplished by using the normal acetonitrile solvent, following with two-1 mL portions of ethyl acetate solvent added directly to the disk.

Data from TABLE II show that Amberchrom CG-161m resin particles with an elution solvent stronger (stronger in the sense of being less polar) than acetonitrile [relative polarities of solvents are given in L. R. Snyder, Journal of Chromatography, 92, 223, (1974), and L. R. Snyder, Journal of Chromatographic Science, 16, 223, (1978)] can give quantitative recoveries of the phenols without addition of acid or salt. This is in contrast to data shown in TABLE I, columns B, C, and D, wherein improved recoveries required salt and/or acid added to the sample liquid. In addition, the data show that these recoveries using media of the invention containing styrene-divinyl benzene resin are strongly dependent on flow rate, indicating kinetics that may be somewhat slow compared to those of conventional $C_{18}$ silica, in which it is possible to process a liter of water in less than 2 minutes with 100% recoveries. This flow rate dependence could be either a function of the relatively large particle size of the Amberchrom CG-161m resin, the structure of the relatively loose (porous) disk, or perhaps is a basic property of the resin's pore structure and/or sorptive interaction.

Data from the one liter sample (column F) also show a surprisingly high capacity of the disk for these compounds. When the percent recoveries shown in column F are multiplied by the total weight of these contaminant compounds fortified into the one liter water sample, the resulting number is the total weight of contaminants retained on the disk. Approximately 60 mg of contaminants were retained on the 240 mg disk. This weight of contaminants is 25 percent of the disk's weight, which is much higher than the usual 5 percent by weight capacity often cited for $C_{18}$ bonded silica.

TABLE I

| | (Comparative) | | | |
|---|---|---|---|---|
| | % Recovery | | | |
| Contaminant | A | B | C | D |
| HMX | 5 | 5 | 12 | 9 |
| phenol | 4 | 5 | 7 | 23 |
| o-cresol | 20 | 26 | 40 | 94 |
| 2-nitrophenol | 35 | 33 | 62 | 90 |
| 2,6-dinitrotoluene | 97 | 100 | 99 | 97 |
| 4,6-dinitro-o-cresol | 14 | 35 | 96 | 94 |
| 2,4-dichlorophenol | 106 | 115 | 95 | 92 |
| 2,4,5-trichlorophenol | 108 | 112 | 94 | 92 |
| 2,4,6-trichlorophenol | 110 | 116 | 94 | 92 |

TABLE II

| | % Recovery | | | |
|---|---|---|---|---|
| Contaminant | E | F | G | H |
| HMX | 122 | 51 | 36 | 55 |
| phenol | 90 | 19 | 28 | 49 |
| o-cresol | 120 | 50 | 40 | 62 |
| 2-nitrophenol | 108 | 85 | 52 | 80 |
| 2,6-dinitrotoluene | 113 | 102 | 66 | 93 |
| 4,6-dinitro-o-cresol | 96 | 60 | 47 | 73 |
| 2,4-dichlorophenol | 107 | 88 | 56 | 86 |
| 4,6-dinitro-o-cresol | 96 | 60 | 47 | 73 |
| 2,4,5-trichlorophenol | 95 | 93 | 61 | 87 |
| 2,4,6-trichlorophenol | 96 | 95 | 62 | 89 |

EXAMPLE 2

A similar set of trials (using disks prepared as in EXAMPLE 1, A and B) was run to evaluate recoveries of the set of compound of Example 1 using stacked disks of the invention. The trial used 100 mL water samples with no acid or salt, and the disks indicated below were stacked one on top of the other and then put in place on the filtration apparatus. Elution was accomplished using two 5-mL portions of acetonitrile solvent, rinsing the glassware, followed by two 1-mL portions of ethyl acetate elution solvent directly onto the disk. Results are given in TABLE III, below. Column I shows the data using $C_{18}$-covalently bond silica on top of the Amberchrom CG-161m resin-containing disk, and eluted with both solvents. Column J is the data from the $C_{18}$-bonded silica disk on top of the Amberchrom CG-161m resin disk, but eluted with only the two 5 mL portions of acetonitrile. Column K is the bottom Amberchrom CG-161m resin disk, separated from the top $C_{18}$-bonded silica disk and eluted With both solvents. Column L is the top $C_{18}$ bonded silica disk, separated from the Amberchrom CG-161m resin disk and eluted with both solvents. The disks from K and L were run stacked together for the extraction step and disks from K and L were then separated for the elution step. Data in column M is the sum of the data in columns K and L, which is the total recovery from the separately eluted disks.

There are some surprising results from using stacked disks. First, data of column J of TABLE III show that acetonitrile solvent eluted the hydrophobic compounds from the $C_{18}$ disk through the Amberchrom CG-161m resin disk. Second, and more importantly, stacking the disks and then separately eluting them individually gave additional information about the types of compounds in each eluting fraction as shown in columns K and L of TABLE III. If a compound was well retained on the top $C_{18}$-bonded silica disk, it was inferred that it was relatively hydrophobic or nonpolar. If, on the other hand, a compound was unretained on the upper $C_{18}$-bonded silica disk, but quantitatively retained on the lower Amberchrom CG-161m resin disk, it was inferred that the compound was relatively polar or hydrophilic. In a further step a ratio can be made of the recovery from the $C_{18}$ disk to the recovery from the Amberchrom CG-161m disk as a qualitative confirmation of the compound's identity. The ratio for the peak from the unknown compound can be compared to the ratio for a known reference compound. This ratio would provide a useful second piece of evidence relating to a compound's identity from the chromatographic peak in addition to the retention data and could be used in either gas chromatography (GC) or HPLC. For this ratio to be effective, the $C_{18}$ disk must be used on top of the Amberchrom CG-161m disk, or all of the compounds would be retained on the top Amberchrom CG-161m disk, giving no additional information to the analyst.

Column N (comparative) lists the data from two $C_{18}$ disks, stacked one on top of the other, and eluted with acetonitrile solvent only. Data shown in column N from the stacked $C_{18}$ disks show a recovery of the poorly retained compounds that was about twice the recovery from a single $C_{18}$ disk (Table I, column A). These data illustrate the utility of using stacked disks as a way to increase recovery and breakthrough volume for poorly retained compounds. In addition, stacked disks can double the capacity of a filtration/extraction trial for samples which have high levels of dissolved organics or are heavily polluted. Finally, the bottom disk of a set of disks can be used to detect an overloading of or breakthrough from the top disk, thus indicating that the analytical data is suspect (the latter is quite common in air sampling, where sampling tubes have backup sections to detect breakthrough).

TABLE III

| | % Recovery | | | | | |
|---|---|---|---|---|---|---|
| Contaminant | I | J | K | L | M | N |
| HMX | 94 | 109 | 81 | 12 | 93 | 17 |
| phenol | 78 | 94 | 55 | 10 | 65 | 18 |
| o-cresol | 91 | 118 | 48 | 34 | 82 | 69 |
| 2-nitrophenol | 89 | 104 | 35 | 47 | 82 | 77 |

TABLE III-continued

| Contaminant | % Recovery I | J | K | L | M | N |
|---|---|---|---|---|---|---|
| 2,6-dinitrotoluene | 91 | 112 | — | 89 | 89 | 99 |
| 4,6-dinitro-o-cresol | 41 | 80 | 41 | 21 | 62 | 29 |
| 2,4-dichlorophenol | 89 | 101 | — | 88 | 88 | 99 |
| 2,4,5-trichlorophenol | 86 | 99 | — | 86 | 86 | 98 |
| 2,4,6-trichlorophenol | 89 | 97 | — | 88 | 88 | 96 |

For 4,6-dinitro-o-cresol it would appear a lower pH would provide more efficient extraction.

EXAMPLE 3

Amberchrom™ CG-71m resin, an acrylic resin bead (Supelco, Bellefonte, Pa.), was evaluated using the contaminants and procedures of Example 1B except that the particles were Amberchrom CG-71m and the amount of lubricant was 40 g. Also tested were disks in which there was a blend of particles: 20% Amberlite XAD-2:80% $C_{18}$-bonded silica. The particles were homogeneously blended into the disk with about 90% particles and 10% PTFE. The 100 mL water samples contained no acid or salt. The elution was accomplished using both acetonitrile and ethyl acetate solvents, as described in EXAMPLE 1. The results are shown in TABLE IV. Data in column P is from Amberchrom™ 71 resin; data in column Q is from the Amberlite XAD-2/$C_{18}$ blend.

Data of TABLE IV show recoveries were good for the Amberchrom™ 71 resin.

TABLE IV

| | % Recovery P | O |
|---|---|---|
| HMX | 101 | 29 |
| phenol | 85 | 18 |
| o-cresol | 125 | 75 |
| 2-nitrophenol | 108 | 102 |
| 2,6-dinitrotoluene | 116 | 111 |
| 4,6-dinitro-o-cresol | 65 | 31 |
| 2,4-dichlorophenol | 103 | 103 |
| 2,4,5-trichlorophenol | 106 | 104 |
| 2,4,6-trichlorophenol | 106 | 104 |

EXAMPLE 4

To conclude the trials on polar compounds, the compounds which worked so well on the $C_{18}$-bonded silica disks (prepared as in Example 1A), i.e., pesticides, were tested with the Amberchrom CG-161m particle-containing disks (prepared as in Example 1B) and Amberchrom CG-71m resin particle-containing disks (prepared as in Example 3) to see if Amberchrom CG-161m and Amberchrom CG-71m resin disks could be used for a series of pollutants or organic compounds in water, with a wide range of polarity and functionality. The size of the water sample was one liter which was fortified with about 100 $\mu$g/L of the three pesticides shown in TABLE V. The water was filtered/extracted rather slowly, since the kinetics of the separation were assumed to be slow with the large resin particles. One liter was filtered in about 2 hours. The elution was done using two 3-mL portions of acetonitrile solvent followed by two 1-mL ethyl acetate solvent on the disk. The only additive in the water was the usual 0.5% methanol for "wetting" purposes. Results are shown in TABLE V. Column R data are from a production $C_{18}$-bonded silica disk (Varian Sample Preparation Products, Harbor City, Calif.). Column S data are from an Amberchrom CG-71m resin disk, and Column T data are from an Amberchrom CG-161m resin disk.

Data of TABLE V show Amberchrom CG-161m and CG-171m resin disks work as well as the $C_{18}$-bonded silica disks for the pesticides, which were chosen for their different functionalities.

TABLE V

| Contaminant | % Recovery R Comparative | S | T |
|---|---|---|---|
| Atrazine | 94 | 88 | 92 |
| Alachlor | 92 | 96 | 135 |
| Diazinon | 99 | 98 | 102 |

EXAMPLE 5

A 25 mm×0.5 mm diameter disk containing macroporous 3–10 micrometer crosslinked styrene-divinylbenzene copolymer (Sarasep, Inc., Santa Clara, Calif.) was placed in a stainless steel holder and used to sample air, as is common practice (see ASTM Method D 4861–88). The disks were prepared using the procedure of Example 1B except the weight of particulate was 32 g, the weight of PTFE emulsion was 16 g, and the weight of lubricant water/isopropanol 50:50 was 40 g. Five hundred nanograms each of five common organophosphorus pesticides were placed in a vapor generator and the vapors were drawn through the disk using a positive-pressure nitrogen flow at a sampling rate of one liter per minute for 18 hours and 30 minutes, making a total volume of 1110 liters.

The disk was then removed from the 25 mm holder and placed in the bottom of a beaker along with 1 mL of ethyl acetate. After 30 minutes with occasional swirling, the ethyl acetate, which had desorbed the pesticides from the disk, was analyzed by gas chromatography with a nitrogen-phosphorus detector. The sampling efficiency (percent recovery) was determined by comparing the peak areas of the sample to those of standards. Results are shown in TABLE VI. With the exception of malathion, which is known to degrade under these conditions, the recoveries indicate that the disk with the crosslinked styrene-divinylbenzene copolymer particulate is effective as an air sampling medium.

This represents a major advance in the practice of air sampling, since the standard procedure outlined in the ASTM procedure (above) calls for large amounts of solvent to pre-extract impurities from the standard polyurethane foam sorbent, and large amounts of solvent to extract the contaminants from the polyurethane foam sorbent after sampling. By using the disk as described above, which uses only a few ml of solvent to pre-extract impurities and one ml of solvent to extract the contaminants, the amount of solvent, time, and labor used can be reduced.

TABLE VI

| Compound | Percent Recovery |
|---|---|
| dichlorvos | 97.8 |
| diazinon | 74.5 |
| parathion | 97.2 |
| malathion | 41.8 |
| chlorpyrifos | 91.4 |

Various modifications and alterations of this invention will become apparent to those skilled in the art without departing from the scope and spirit of this invention, and it should be understood that this invention is not to be unduly limited to the illustrative embodiments set forth herein.

We claim:

1. A method of isolating at least one organic contaminant from a fluid comprising the step of:

passing a fluid containing at least one contaminant through at least one solid phase extraction medium comprising (a) a PTFE fibril matrix, and (b) sorptive particles *that are essentially non-water-swellable* enmeshed in said matrix comprising (1) more than 30 and up to 100 weight percent of porous organic particles selected from the group consisting of a copolymer of styrene divinylbenzene, a poly(meth)acrylic acid ester, a polydivinylbenzene, or a derivative of any of the foregoing, and (2) less than 70 to 0 weight percent of porous, organic-coated or uncoated, inorganic particles, the ratio of sorptive particles to PTFE being in the range of 40:1 to 1:4 by weight.

2. The method according to claim 1 further comprising the step of eluting said at least one contaminant from said extraction medium with an appropriate solvent.

3. The method according to claim 1 wherein said organic-coated inorganic particles comprise at least one of silica, alumina, titania, or zirconia to which is bonded an aliphatic or aromatic organic group.

4. The method according to claim 3 wherein said particle is silica and wherein said organic group is selected from the group consisting of amino, hydroxyl, chiral, cyano, cyclohexyl, phenyl, ethyl, butyl, octyl, and octadecyl.

5. The method according to claim 1 wherein the ratio of organic to inorganic particles by weight is 35 to 100:0 to 65.

6. The method according to claim 1 wherein the ratio of organic to inorganic particles by weight is 50 to 100:0 to 50.

7. The method according to claim 1 wherein said medium is a sheet material.

8. The method according to claim 1 wherein said contaminant is a pesticide.

9. The method according to claim 1 wherein said contaminant is a residue of an explosive.

10. The method according to claim 1 wherein said contaminant is a phenolic compound.

11. The method according to claim 1 wherein said organic particulate is a copolymer of styrene divinylbenzene and said inorganic particulate is $C_{18}$-covalently bonded silica.

12. The method according to claim 1 wherein said contaminant is a polar or semi-polar substance.

13. The method according to claim 1 wherein said organic particles are a copolymer of styrene divinylbenzene or a derivative thereof.

14. The method according to claim 1 wherein said organic particles are a poly(meth)acrylic acid ester or a derivative thereof.

15. The method according to claim 1 wherein said organic particles are a polydivinylbenzene or a derivative thereof.

16. A solid phase extraction medium comprising (a) a PTFE fibril matrix, and (b) sorptive particles *that are essentially non-water-swellable* enmeshed in said matrix comprising (1) more than 30 and up to 100 weight percent of porous organic particles selected from the group consisting of a copolymer of styrene divinylbenzene, a poly(meth)acrylic acid ester, a polydivinylbenzene, or a derivative of any of the foregoing, and (2) less than 70 to 0 weight percent of porous, organic-coated or uncoated, inorganic particles, the ratio of sorptive particles to PTFE being in the range of 40:1 to 1:4 by weight.

17. The medium according to claim 16 wherein said organic particles are present in the range of 35 to 100 weight percent and said coated or uncoated inorganic particles are present in the range of 0 to 65 weight percent.

18. The medium according to claim 16 wherein in said medium said organic particles are present in the range of 50 to 100 weight percent and said coated or uncoated inorganic particles are present in the range of 0 to 50 weight percent.

19. The medium according to claim 16 wherein said organic particles are present in the range of 35 to 100 weight percent and said coated or uncoated inorganic particles are present in the range of 0 to 65 weight percent.

20. The medium according to claim 16 wherein said organic particles are present in the range of 50 to 100 weight percent and said coated or uncoated inorganic particles are present in the range of 0 to 50 weight percent.

21. The medium according to claim 16 wherein said contaminant is a polar or semi-polar substance.

22. The medium according to claim 16 wherein said organic particles are a copolymer of styrene divinylbenzene or a derivative thereof.

23. The medium according to claim 16 wherein said organic particles are a poly(meth)acrylic acid ester or a derivative thereof.

24. The medium according to claim 16 wherein said organic particles are a polydivinylbenzene or a derivative thereof.

25. The medium according to claim 16 wherein said organic-coated inorganic particles comprise at least one of silica, alumina, titania, or zirconia to which is bonded an aliphatic or aromatic organic group.

26. The medium according to claim 25 wherein said particle is silica and wherein said organic group is selected from the group consisting of amino, hydroxyl, cyano, cyclohexyl, phenyl, ethyl, butyl, octyl, and octadecyl.

[27. The medium according to claim 16 wherein said sorptive particles are non-swellable.]

28. A stack of at least 2 disks wherein at least one disk is a solid phase extraction [medium] *material* comprising (a) a PTFE fibril matrix, and (b) essentially non-water-swellable [and non-organic liquid swellable] sorptive particles enmeshed in said matrix comprising (1) more than 30 and up to 100 weight percent of porous organic particles, and (2) less than 70 to 0 weight percent of porous, organic-coated or uncoated, inorganic particles, the ratio of sorptive particles to PTFE being in the range of 40:1 to 1:4 by weight, and wherein in at least one of said disks said organic particles are selected from the group consisting of a copolymer of styrene divinylbenzene, a poly(meth)acrylic acid ester, a polydivinylbenzene, or a derivative of any of the foregoing.

29. The stack of disks according to claim 28 wherein the media of said disks are of the same composition.

30. The stack of disks according to claim 28 wherein the media of at least two of said disks differ from each other in composition.

31. The stack of disks according to claim 28 wherein at least one disk comprises at least one of $C_2$–$C_8$, and $C_{18}$-covalently bonded silica particles.

32. The stack of disks according to claim 28 wherein at least one disk comprises inorganic particles to which are bonded organic groups selected from the group consisting of amino, cyano, hydroxyl, cyclohexyl, phenyl, ethyl, butyl, octyl, octadecyl, and chiral groups.

33. A method of isolating at least one organic contaminant from a liquid comprising the step of:

passing a liquid containing at least one contaminant through at least one solid phase extraction medium comprising (a) a PTFE fibril matrix, and (b) sorptive particles *that are essentially non-water-swellable* enmeshed in said matrix comprising (1) more than 30 and up to 100 weight percent of porous organic particles selected from the group consisting of a copolymer of styrene divinylbenzene, a poly(meth)acrylic acid ester, a polydivinylbenzene, or a derivative of any of the foregoing, and (2) less than 70 to 0 weight percent of porous, organic-coated or uncoated, inorganic particles, the ratio of sorptive particles to PTFE being in the range of 40:1 to 1:4 by weight.

34. The method according to claim 33 further comprising the step of eluting said at least one contaminant from said extraction medium with an appropriate solvent.

35. A method of isolating at least one organic contaminant from a fluid comprising the step of:

passing a fluid containing at least one contaminant through at least one solid phase extraction medium comprising (a) a PTFE fibril matrix, and (b) sorptive particles *that are essentially non-water-swellable* enmeshed in said matrix comprising (1) more than 30 and up to 100 weight percent of porous organic particles selected from the group consisting of a copolymer of styrene divinylbenzene, a poly(meth)acrylic acid ester, a polydivinylbenzene, or a derivative of any of the foregoing, and (2) less than 70 to 0 weight percent of porous, organic-coated or uncoated, inorganic particles, the ratio of sorptive particles to PTFE being in the range of 40:1 to 1:4 by weight, and eluting said at least one contaminant from said extraction medium with an appropriate solvent.

36. The medium according to claim 16 wherein the molecules of said organic coating of said inorganic particles are chiral.

*37. An extraction medium comprising*

*(a) a PTFE fibril matrix, and*

*(b) sorptive particles enmeshed in said matrix having a change in volume of less than 0.5 when swollen in water, said sorptive particles comprising*

*(1) more than 30 and up to 100 weight percent of porous organic particles selected from the group consisting of a copolymer of styrene and divinylbenzene, a poly(metha)acrylic acid ester, a polydivinylbenzene, or a derivative of any of the foregoing, and*

*(2) less than 70 to 0 weight percent of porous, organic-coated or uncoated, inorganic particles, the ratio of sorptive particles to PTFE being in the range of 40:1 to 1:4 by weight,*

*said medium being a solid phase extraction medium.*

*38. The extraction medium according to claim 37 wherein said sorptive particles have a change in volume of less than 0.1 when swollen.*

*39. The extraction medium according to claim 37 wherein said sorptive particles have a change in volume of less than 0.01 when swollen.*

*40. The extraction medium according to claim 37 wherein said porous organic particles have an average size in the range of 0.1 to 30 micrometers.*

*41. An extraction medium comprising*

*(a) a PTFE fibril matrix, and*

*(b) sorptive particles having a water sorptive capacity of less than 25 weight percent enmeshed in said matrix comprising*

*(1) more than 30 and up to 100 weight percent of porous organic particles selected from the group consisting of a copolymer of styrene and divinylbenzene, a poly(meth)acrylic acid ester, a polydivinylbenzene, or a derivative of any of the foregoing, and*

*(2) less than 70 to 0 weight percent of porous, organic-coated or uncoated, inorganic particles,*

*the ratio of sorptive particles to PTFE being in the range of 40:1 to 1:4 by weight,*

*said medium being a solid phase extraction medium.*

*42. The extraction medium according to claim 41 wherein said sorptive particles have a water sorptive capacity of less than 5% by weight.*

*43. An extraction medium comprising*

*(a) a PTFE fibril matrix, and*

*(b) highly crosslinked sorptive particles enmeshed in said matrix comprising*

*(1) more than 30 and up to 100 weight percent of porous organic particles selected from the group consisting of a copolymer of styrene and divinylbenzene, a poly(meth)acrylic acid ester, a polydivinylbenzene, or a derivative of any of the foregoing, and*

*(2) less than 70 to 0 weight percent of porous, organic-coated or uncoated, inorganic particles,*

*the ratio of sorptive particles to PTFE being in the range of 40:1 to 1:4 by weight,*

*said medium being a solid phase extraction medium.*

*44. The extraction medium according to claim 43 wherein said porous organic particles having an average size in the range of 0.1 to 30 micrometers.*

*45. A disk comprising a solid phase extraction medium including*

*(a) a PTFE fibril matrix, and*

*(b) sorptive particles that are essentially non-water-swellable enmeshed in said matrix comprising*

*(1) more than 30 and up to 100 weight percent of porous organic particles, and*

(2) *less than 70 to 0 weight percent of porous organic-coated or uncoated, inorganic particles,*

*the ratio of sorptive particles to PTFE being in the range of 40:1 to 1:4 by weight, and wherein in said disk said organic particles are selected from the group consisting of a copolymer of styrene and divinylbenzene, a poly(meth)acrylic acid ester, a polydivinylbenzene, or derivative of any of the forgoing.*

*46. The method according to claim 1 wherein said fluid passes through said solid phase extraction medium at an angle of 90 degrees to the surface of said medium.*

*47. The method according to claim 1 wherein said method further comprises the step of chromatographically analyzing said at least one contaminant after isolation from said fluid.*

* * * * *

UNITED STATES PATENT AND TRADEMARK OFFICE

CERTIFICATE OF CORRECTION

PATENT NO. : RE 36,811
DATED : January 18, 1994
INVENTOR(S) : Markell, Craig G.

It is certified that error appears in the above-identified patent and that said Letters Patent is hereby corrected as shown below:

Title page,
Item [21], Application No.: delete "08/930,714" and insert in place thereof -- 07/930,714 --.

Column 1,
Line 15, delete "polytetrefluoroethylene" and insert in place thereof -- polytetrafluoroethylene --.

Column 4,
Line 59, delete "hdyroxyl" and insert in place thereof -- hydroxyl --.

Column 9,
Line 28, delete "the" and insert in place thereof -- The --.

Column 12,
Line 19, delete "part" and insert in place thereof -- apart --.

Column 14,
Line 5, delete "With" and insert in place thereof -- with --.

Column 17,
Line 26, following "styrene" and before "divinylbenzene" insert -- and --.

Column 18,
Line 9, following "styrene" and before "divinylbenzene" insert -- and --.

Column 20,
Line 2, delete "poly(metha)acrylic" and insert in place thereof -- poly(meth)acrylic --.
Line 58, delete "having" and insert in place thereof -- have --.

Signed and Sealed this

Nineteenth Day of November, 2002

*Attest:*

*Attesting Officer*

JAMES E. ROGAN
*Director of the United States Patent and Trademark Office*